(12) United States Patent
Yaniv et al.

(10) Patent No.: US 11,653,871 B2
(45) Date of Patent: May 23, 2023

(54) ATRIAL FIBRILLATION PREDICTION USING HEART RATE VARIABILITY

(71) Applicant: TECHNION RESEARCH & DEVELOPMENT FOUNDATION LIMITED, Haifa (IL)

(72) Inventors: Yael Yaniv, Haifa (IL); Noam Keidar, Haifa (IL); Yonatan Elul, Tiberias (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 142 days.

(21) Appl. No.: 16/978,724

(22) PCT Filed: Mar. 7, 2019

(86) PCT No.: PCT/IL2019/050256
§ 371 (c)(1),
(2) Date: Sep. 7, 2020

(87) PCT Pub. No.: WO2019/171384
PCT Pub. Date: Sep. 12, 2019

(65) Prior Publication Data
US 2021/0282692 A1  Sep. 16, 2021

Related U.S. Application Data

(60) Provisional application No. 62/639,543, filed on Mar. 7, 2018.

(51) Int. Cl.
*A61B 5/00* (2006.01)
*A61B 5/361* (2021.01)
*A61B 5/024* (2006.01)

(52) U.S. Cl.
CPC .......... *A61B 5/361* (2021.01); *A61B 5/02405* (2013.01); *A61B 5/7267* (2013.01)

(58) Field of Classification Search
CPC ...................................................... A61B 5/361
(Continued)

(56) References Cited

U.S. PATENT DOCUMENTS 9,320,448 B2 * 4/2016 Xi .......................... A61B 5/361
2009/0264783 A1 * 10/2009 Xi .......................... A61B 5/361
600/521

(Continued)

FOREIGN PATENT DOCUMENTS

CN  104367318 A  2/2015
CN  106073755 A  11/2016

(Continued)

OTHER PUBLICATIONS

Fioranelli M, Piccoli M, Mileto GM, Sgreccia F, Azzolini P, Risa MP, Francardelli RL, Venturini E, Puglisi A. Analysis of heart rate variability five minutes before the onset of paroxysmal atrial fibrillation. Pacing Clin Electrophysiol. May 1999.

(Continued)

*Primary Examiner* — Nicole F Lavert
(74) *Attorney, Agent, or Firm* — The Roy Gross Law Firm, LLC; Roy Gross

(57) ABSTRACT

A method comprising: receiving a plurality of data segments each representing human cardiac activity; calculating, from each of said data segments, a first value representing a distribution of a heart rate variability (HRV) parameter; acquiring a signal representing cardiac activity in a patient; deriving a second value representing distribution of an HRV parameter in said signal; and indicating an atrial fibrillation (AF) event in said patient, when a difference between said first and second values is above a predetermined threshold.

18 Claims, 13 Drawing Sheets

(58) Field of Classification Search
USPC .......................................................... 600/518
See application file for complete search history.

(56) References Cited

U.S. PATENT DOCUMENTS

| | | | | |
|---|---|---|---|---|
| 2010/0056940 | A1* | 3/2010 | Moorman | A61B 5/7242 600/509 |
| 2012/0296175 | A1* | 11/2012 | Poh | A61B 5/02405 600/483 |
| 2016/0081566 | A1* | 3/2016 | Xu | A61B 8/02 600/509 |
| 2016/0135706 | A1 | 5/2016 | Sullivan et al. | |
| 2016/0331247 | A1 | 11/2016 | Albert | |

FOREIGN PATENT DOCUMENTS

| | | | |
|---|---|---|---|
| WO | WO-2005067790 A1 * | 7/2005 | ......... A61B 5/02405 |
| WO | 2015089484 A1 | 6/2015 | |
| WO | 2016183515 A1 | 11/2016 | |
| WO | 2019071201 A1 | 4/2019 | |

OTHER PUBLICATIONS

Goldberger AL, Rigney DR, West BJ. Chaos and fractals in human physiology. Sci Am. Feb. 1990;262(2):42-9.
Papaioannou, Vasilios et al. "Association of heart rate variability and inflammatory response in patients with cardiovascular diseases: current strengths and limitations." Frontiers in physiology vol. 4 174. Jul. 10, 2013.
Stefanie Hillebrand, Karin B. Gast, Renée de Mutsert, Cees A. Swenne, J. Wouter Jukema, Saskia Middeldorp, Frits R. Rosendaal, Olaf M. Dekkers, Heart rate variability and first cardiovascular event in populations without known cardiovascular disease: meta-analysis and dose-response meta-regression, EP Europace, vol. 15, Issue 5, May 2013.
Wolf, Philip A., Robert D. Abbott, and William B. Kannel. "Atrial fibrillation as an independent risk factor for stroke: the Framingham Study." stroke 22, No. 8 (1991).
Feinberg WM, Blackshear JL, Laupacis A, Kronmal R, Hart RG. Prevalence, Age Distribution, and Gender of Patients Nith Atrial Fibrilation: Analysis and Implications. Arch Intern Med. 1995.
Go AS, Hylek EM, Phillips KA, et al. Prevalence of Diagnosed Atrial Fibrillation in Adults: National Implications for Rhythm Management and Stroke Prevention: the AnTicoagulation and Risk Factors In Atrial Fibrillation (ATRIA) Study. JAMA. 2001.
Benjamin EJ, Chen PS, Bild DE, Mascette AM, Albert CM, Alonso A, Calkins H, Connolly SJ, Curtis AB, Darbar D, Ellinor PT, Go AS, Goldschlager NF, Heckbert SR, Jalife J, Kerr CR, Levy D, Lloyd-Jones DM, Massie BM, Nattel S, Olgin JE, Packer DL, Po SS, Tsang TS, Van Wagoner DR, Waldo AL, Wyse DG. Prevention of atrial fibrillation: report from a national heart, lung, and blood institute workshop. Circulation. Feb. 3, 2009;119(4):606-18.
Bergfeldt L, Haga Y. Power spectral and Poincare plot characteristics in sinus node dysfunction. J Appl Physiol (1985). Jun. 2003;94(6):2217-24.
Akyürek, ÖMer, Erdem Diker, Muharrem Güldal, and Derviş Oral. "Predictive value of heart rate variability for the recurrence of chronic atrial fibrillation after electrical cardioversion." Clinical Cardiology: An International Indexed and Peer-Reviewed Journal for Advances in the Treatment of Cardiovascular Disease 26, No. 4 (2003): 196-200.
Vaziri, Sonya M., Martin G. Larson, Emelia J. Benjamin, and Daniel Levy. "Echocardiographic predictors of nonrheumatic atrial fibrillation. The Framingham Heart Study." Circulation 89, No. 2 (1994): 724-730.
Seaborn GE, Todd K, Michael KA, Baranchuk A, Abdollah H, Simpson CS, Aki SG, Redfeam DP. Heart rate variability and procedural outcome in catheter ablation for atrial fibrillation. Ann Noninvasive Electrocardiol. Jan. 2014;19 (1):23-33.
Andrew Y. Ng, Michael L Jordan, and Yair Weiss. 2001. On spectral clustering: analysis and an algorithm. In Proceedings of the 14th International Conference on Neural Information Processing Systems: Natural and Synthetic (NIPS'01). MIT Press, Cambridge, MA, USA, 849-856.
Costa M, Goldberger AL, Peng CK. Multiscale entropy analysis of complex physiologic time series. Phys Rev Lett. Aug. 5, 2002;89(6):068102.
Shin, D.G., Yoo, C.S., Yi, S.H., Bae, J.H., Kim, Y.J., Park, U.S., & Hong, G.R. (2006). Prediction of Paroxysmal Atrial Fibrillation Using Nonlinear Analysis of the R-R Interval Dynamics Before the Spontaneous Onset of Atrial Fibrillation. Circulation Journal, 70(1), 94-99.
Bettoni M, Zimmermann M. Autonomic tone variations before the onset of paroxysmal atrial fibrillation. Circulation. Jun. 11, 2002;105(23):2753-9.
Vikman S, Mäkikallio TH, Yli-Mäyry S, Pikkujämsä S, Koivisto AM, Reinikainen P, Airaksinen KE, Huikuri HV. Altered complexity and correlation properties of R-R interval dynamics before the spontaneous onset of paroxysmal atrial fibrillation. Circulation. Nov. 16, 1999;100(20):2079-84.
Mohebbi, M., & Ghassemian, H. (2012). Prediction of paroxysmal atrial fibrillation based on non-linear analysis and spectrum and bispeclium features of the heart rate variability signal. Computer Methods and Programs in Biomedicine, 105(1), 40-49.
Chesnokov YV. Complexity and spectral analysis of the heart rate variability dynamics for distant prediction of paroxysmal atrial fibrillation with artificial intelligence methods. Artif Intell Med. Jun. 2008;43(2):151-65.
Yaniv Y, Lyashkov AE, Lakatta EG. Impaired signaling intrinsic to sinoatrial node pacemaker cells affects heart rate variability during cardiac disease. J Clin Trials. Mar. 2014;4(1):152.
Goldberger AL, Amaral LA, Glass L, Hausdorff JM, Ivanov PC, Mark RG, Mietus JE, Moody GB, Peng CK, Stanley HE. PhysioBank, PhysioToolkit, and PhysioNet: components of a new research resource for complex physiologic signals. Circulation. Jun. 13, 2000;101(23):E215-20.
1. Rosenberg, A.A. (2018), "Non-lnvasive In-Vivo Analysis of Intrinsic Clock-Like Pacemaker Mechanisms: Decoupling Neural Input Using Heart Rate Variability Measurements" (master's thesis).
PCT Search Report of PCT/IL2019/050256 Completed Jul. 9, 2019; dated Jul. 9, 2019 4 pages.
Written Opinion of PCT/IL2019/050256 Completed Jul. 9, 2019; dated Jul. 9, 2019 5 pages.

\* cited by examiner

ATRIAL FIBRILLATION PREDICTION USING HEART RATE VARIABILITY

CROSS-REFERENCE TO RELATED APPLICATIONS

This application is a National Phase of PCT Patent Application No. PCT/IL2019/050256 having International filing date of Mar. 7, 2019, which claims the benefit of priority of U.S. Provisional Patent Application No. 62/639,543 filed Mar. 7, 2018. The content of the above applications is incorporated herein by reference in its entirety.

BACKGROUND

The heart rate never reaches a steady state, as it is controlled by complex, dynamic, chaotic processes and oscillates at different periods over different, continuously shifting time scales (Goldberger A L et al. Sci Am. 1990; 262:42-9). Therefore, it is not surprising that ECG recordings in mammals, even under resting conditions, reveal complex beat-to-beat variations in heartbeat intervals (Papaioannou V et al. Frontiers in physiology. 2013; 4:174). While a decrease in this complexity in humans with cardiovascular disease correlates with increased morbidity and mortality (Hillebrand S et al. Europace. 2013; 15:742-9), an increase in heart rate variability (HRV) above a certain threshold, or in mathematical terms, in system entropy, leads to the abnormal electrical impulse conductance that is defined as fibrillation.

Cardiac fibrillation is one of the leading causes of morbidity and mortality in the developed world, where atrial fibrillation (AF) is the most common sustained arrhythmia (Wolf P A et al. Stroke. 1991; 22:983-8), affecting approximately 2.2 million patients in the United States, and its prevalence increases with age (Feinberg W M et al. Archives of internal medicine. 1995; 155:469-73). Although AF is not considered a life-threating arrhythmia, it affects the circulatory system of patients and their general health and quality of life; further, it poses a significant burden on the healthcare system (Feinberg W M et al. Archives of internal medicine. 1995; 155:469-73): e.g., AF is a significant risk factor for stroke, with about 15% of strokes occurring in people with AF (Go et al. JAMA. 2001; 285:2370-5). Unfortunately, currently available drug treatments for AF are less than satisfactory. An expert panel convened by the Heart, Lung and Blood Institute to resolve this issue determined that "AF detection by using emerging methods and technologies" constitutes an important future direction in preventing AF (Benjamin E J et al. Circulation. 2009; 119:606-18). To date, there is no effective clinical method for early prediction and precise identification of AF events.

Interestingly, while persistent AF is associated with an increased HRV on average (Bergfeldt L et al. J Appl Physiol. 2003; 94:2217-24), reduced HRV indices are observed just prior to arrhythmogenic events (Akyurek O et al. Clinical cardiology. 2003; 26:196-200). Although the correlation between changes in heart beat complexity and prevalence of AF has been known for more than three decades (Akyurek O et al. Clinical cardiology. 2003; 26:196-200; Vaziri S M et al. Circulation. 1994; 89:724-30; Seaborn G E et al. Annals of noninvasive electrocardiology: the official journal of the International Society for Holter and Noninvasive Electrocardiology, Inc. 2014; 19:23-33), a method to detect HRV changes on line and in short period before AF event occurs does not exist.

SUMMARY

The following embodiments and aspects thereof are described and illustrated in conjunction with systems, tools and methods which are meant to be exemplary and illustrative, not limiting in scope.

There is provided, in an embodiment, a method comprising receiving a plurality of data segments each representing human cardiac activity; calculating, from each of said data segments, a first value representing a distribution of a heart rate variability (HRV) parameter; acquiring a signal representing cardiac activity in a patient; deriving a second value representing distribution of an HRV parameter in said signal; and indicating an atrial fibrillation (AF) event in said patient, when a difference between said first and second values is above a predetermined threshold.

There is also provided in an embodiment, a system comprising at least one hardware processor; and a non-transitory computer-readable storage medium having stored thereon program instructions, the program instructions executable by the at least one hardware processor to: receive a plurality of data segments each representing human cardiac activity, calculate, from each of said data segments, a first value representing a distribution of a heart rate variability (HRV) parameter, acquire a signal representing cardiac activity in a patient, derive a second value representing distribution of an HRV parameter in said signal, and indicate an atrial fibrillation (AF) event in said patient, when a difference between said first and second values is above a predetermined threshold.

There is further provided, in an embodiment, a computer program product comprising a non-transitory computer-readable storage medium having program instructions embodied therewith, the program instructions executable by at least one hardware processor to: receive a plurality of data segments each representing human cardiac activity; calculate, from each of said data segments, a first value representing a distribution of a heart rate variability (HRV) parameter; acquire a signal representing cardiac activity in a patient; derive a second value representing distribution of an HRV parameter in said signal; and indicate an atrial fibrillation (AF) event in said patient, when a difference between said first and second values is above a predetermined threshold.

In some embodiments, said plurality of data segments represent cardiac activity in a plurality of subjects.

In some embodiments, at least some of said data segments are acquired from said patient.

In some embodiments, said HRV parameter is an entropy parameter.

In some embodiments, said entropy parameter is modified Shannon entropy.

In some embodiments, said calculating comprises calculating a distribution of said HRV parameter in all said data segments.

In some embodiments, each of said data segments is acquired over a period of between 1 and 10 minutes.

In some embodiments, said signal is acquired over a period of between 0.5 and 5 minutes.

In some embodiments, the method further comprises training, and the program instructions are further executable to train, at a training stage, a machine learning classifier on a training set comprising: (i) said plurality of data segment, wherein at least some of said segments comprise cardiac activity reflecting an arrythmia event, and (ii) labels indicating the occurrence of an arrythmia event in said cardiac activity.

In some embodiments, said data segments are labelled with said labels.

In some embodiments, said indicating is performed by applying, at an inference stage, said machine learning classifier to said signal, to indicate an AF event in said patient.

In some embodiments, said indicating comprises at least one of detecting an ongoing AF event, and predicting an upcoming AF event.

In some embodiments, said upcoming AF event occurs between 1 and 5 minutes after said indicating.

In some embodiments, said detecting is based, at least in part, on calculating statistical estimators of said distribution.

In some embodiments, said statistical estimators comprise at least standard deviation and deviation from normal distribution.

In some embodiments, said deviation from normal distribution is based on the Kolmogorov-Smirnov statistic.

In some embodiments, the method further comprises applying, and the program instructions are further executable to apply, a clustering algorithm to said plurality of data segments, to cluster at least some of said data segments based, at least in part, on said HRV parameter. In some embodiments, said clustering algorithm is a spectral clustering algorithm.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
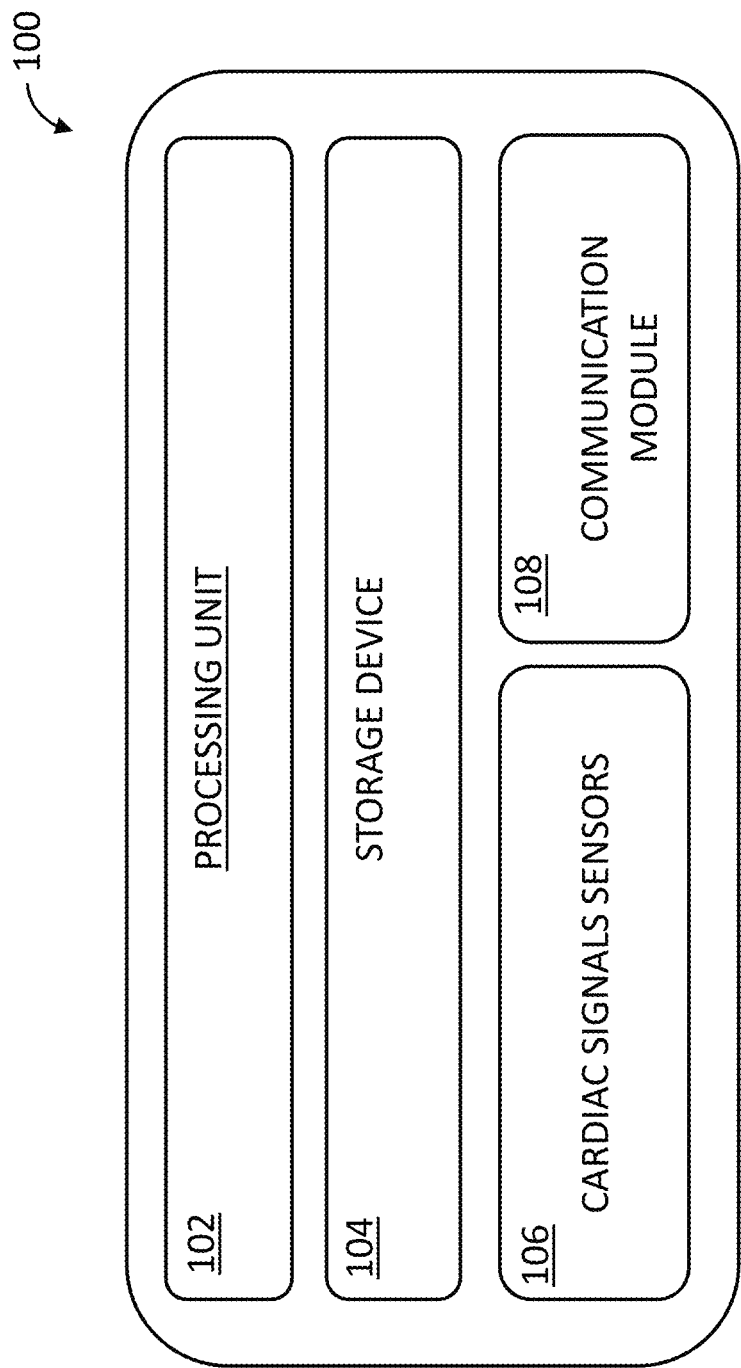
FIG. 1 is a block diagram of a system for predicting and/or detecting atrial fibrillation or other irregular regularity, according to an embodiment.

A system and method are disclosed herein for detecting and/or predicting atrial fibrillation (AF) or other irregular regularity. In some embodiments, the present invention provides for real-time prediction or detection of AF or other irregular regularity by employing an algorithm based on pattern classification of the distribution of a modified Shannon entropy of beating intervals of heart beats intervals. The present method and system produce a real-time alarm when certain changes occur in the modified Shannon entropy of a patient.

The present invention is based on the finding that persistent AF is associated with an increased HRV on average (L. Bergfeldt and Y. Haga, "Power spectral and Poincare plot characteristics in sinus node dysfunction," *J. Appl. Physiol.*, vol. 94, no. 6, pp. 2217-2224, 2003). However, reduced HRV indices are observed just prior to events (O. Akyurek, E. Diker, M. Guldal, and D. Oral, "Predictive value of heart rate variability for the recurrence of chronic atrial fibrillation after electrical cardioversion," *Clin Cardiol*, vol. 26, no. 4, pp. 196-200, 2003). Therefore, an atypical decrease in HRV might be predictive for an upcoming episode of AF, and thus a useful marker to be used in the detection, prevention, research and treatment of AF.

The present invention provides clinical and diagnostic tools for early prediction and detection of AF events by examining changes in HRV. Real-time analysis of HRV of a patient, based on short segments of heartbeat intervals, according to the present method may help to detect and prevent AF events, thereby reducing the probability of associated events, such as strokes. In some embodiments, the disclosed invention allows for prediction of AF events shortly (e.g., 5 min.) before they occur. Early prediction of AF events thus will allow to determine which hemodynamic, mechanical or electrical parameters change just before each episode, and help during ablation procedure.

The present invention can be implemented, for example, as an early detection and prediction system for atrial fibrillation based on continuous heart rate monitoring, as well as for early prediction of arrhythmia episodes in general. In some embodiments, heart beat segments can be acquired from a mobile device, a wearable device, a device that is used to monitor or diagnose medical conditions by medical experts, and/or based on a smart implantable cardiac defibrillator. Because the disclosed method provides for quantifying the HRV accurately based on relatively short segments of heart beats, it can be implemented based on, e.g., a remote ECG acquiring system. Thus, the present method can provide for efficient and cost-effective local and/or remote monitoring of multiple AF patients.

In some embodiments, the present disclosure can be implemented, for example, as a diagnostic system used for assessing the underlying etiology and/or the arrythmia profile of each patient's AF events, allowing personalized treatment.

In some embodiments, methods for predicting and/or detecting AF according to the present disclosure comprise a first step of acquiring and/or receiving one or more prerecorded baseline segments of cardiac activity comprising multiple heart beat intervals of a subject. The baseline segments comprise a plurality of heart beat intervals taken, e.g., at rest, when no arrythmia event was in progress. In some embodiments, the recording of the baseline signal is performed over a period of, e.g., 1 to 10 minutes. A modified Shannon entropy distribution and/or other HRV indices are may then be calculated for the baseline signal. In some embodiments, the present method further comprises calculating a difference in Shannon entropies between every two or more consecutive heart beat intervals of the baseline signal, wherein the calculation of the baseline distribution is based on the calculated differences in Shannon entropies.

In some embodiments, the modified Shannon Entropy is used to separate patients into groups by, e.g., Spectral Clustering.

In real time, a second, shorter, segment of the patient cardiac activity measurement is acquired (the "real-time segment"), wherein a modified Shannon entropy distribution and/or other HRV indices are calculated for the real-time segment as well. The distributions of the baseline and real-time segments are compared to one another. In some embodiments, when a difference in distribution width between the baseline and second segments is above a predetermined threshold, an AF event is predicted and/or detected. In some embodiments, the recording of the real-time segment is performed over a period of 30 seconds to 5 minutes.

In some embodiments, the present disclosure may be implemented as a machine leanring classifier trained on a training set comprising a plurality of cardiac activity segments acquired from a population of subjects, wherein at an inference stage the classifier may be configured to predict and/or detect AF event in a real-time segment acquired from a monitored subject.

Accordingly, in some embodiments, a machine leanring classifier may be trained, e.g., on a training set comprising a plurality of recorded baseline segments measurements from, e.g., a group of subjects. In some embodiments, the baseline segments may comprise a plurality of heart beat intervals of each subject taken, e.g., at rest, when no arrythmia event was in progress. In some embodiments, each segment may comprise, e.g., 1 to 10 minutes of recorded cardiac activity. In some embodiments, an existing database of cardiac activity recordings form a plurality of subjects may comprise at least a portion of the training set. In some embodiments, a modified Shannon entropy distribution and/or other HRV indices are may be derived for each segment within the training set. In some embodiments, modified Shannon entropy may be derived, e.g., by calculating a difference in Shannon entropies between every two or more consecutive heart beat intervals of the baseline signal.

In some embodiments, the training set may be labelled with appropriate labels indicating the existence of an AF event within each segment. In some embodiments, the machine learning classifier may be trained on the training set to classify a segment of cardiac activity as indicative of a concurrent and/or imminent (e.g., within a time horizon of 1-5 mins.) AF event. In some embodiments, a trained classifier of the present disclosure may be used to detect and or predict an AF event, based, at least in part, on a segment of cardiac activity measurement acquired in real time from a subject, wherein the segment may comprise a recording of cardiac activity over a period of 30 seconds to 5 minutes.

With reference to FIG. 1, in some embodiments, an exemplary system 100 in accordance with the present disclosure comprises processing unit 102, comprising at least one hardware processor. Processing unit 102 is communicatively connected to a non-transient computer readable storage device 104. Processing unit 102 is configured to automatically control the operation of system 100, based on one or more applications, sets of software instructions, and algorithms stored storage device 104. Storage device 104 may be configured to have stored thereon digital representations of cardiac signals and/or measurements. In some embodiments, processing unit 102 is configured to receive and process one or more cardiac signals and/or measurements collected by one or more cardiac signal sensors 106. System 100 may further comprise a communication module 108, which may be configured to connect system 100 through a communication network, such as the Internet, a local area network, a wide area network, and/or a wireless network. For example, system 100 may be configured to receive cardiac signals from a remote acquisition unit over a network via communication module 108. System 100 described herein is only an exemplary embodiment, and may have more or fewer components than shown, may combine two or more components, or a may have a different configuration or arrangement of the components. The various components of system 100 may be implemented in hardware, software, or a combination of both hardware and software. According to various other embodiments, processing unit 102 or processing tasks performed thereby may be implemented by a handheld or worn computing device such as, but not limited to, a smart phone, a tablet computer, a notepad computer, smart watch, and the like. In addition, aspects of the present system which can be implemented by computer program instructions, may be executed on a general-purpose computer, a special-purpose computer, or other programmable data processing apparatus.

Figure 2:
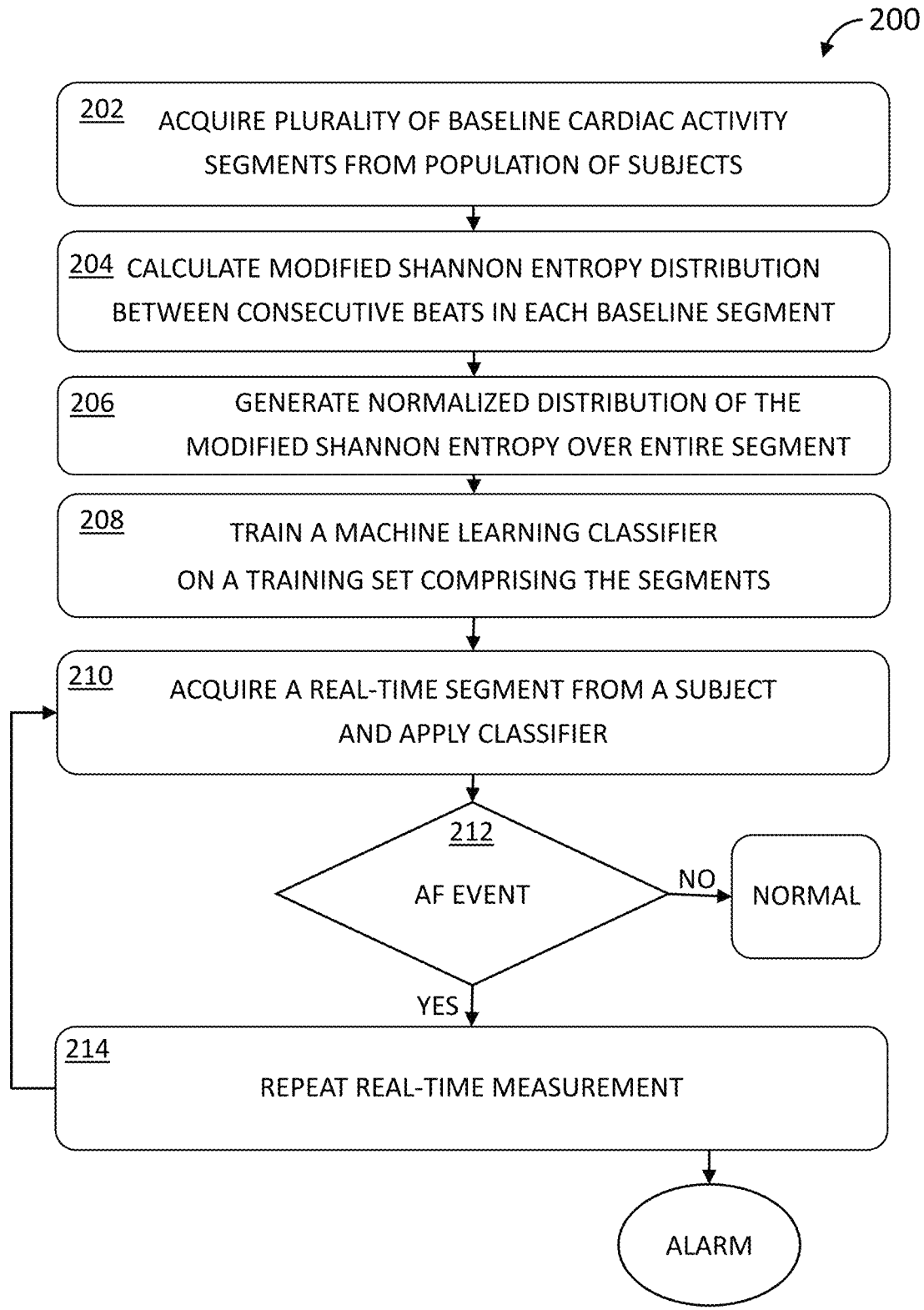
FIG. 2 is a flowchart of a method for predicting and/or detecting atrial fibrillation or other irregular regularity, according to an embodiment.

FIG. 2 is a flowchart illustrating the functional steps of an exemplary prediction and/or detection machine leanring classifier 200, according to some embodiments of the present disclosure. Classifier 200 is configured to calculate HRV over relatively short real-time segments of heart beat, based on pattern classification of distribution of the modified Shannon entropy of beating intervals. Classifier 200 works in two stages: a learning stage (steps 202-206) and an inference stage (steps 208-214).

At a learning stage, starting at 202, a training set of baseline cardiac activity segments of a single or a plurality of subjects may be acquired or received. The baseline segments can be acquired using an ECG and/or similar acquiring methodology from the subjects at rest. In some embodiments, the baseline segments comprise a segment of ECG and/or other bio-signal measurement which can be used to calculate the heart beating intervals (e.g., saturated oxygen, pulse detector, blood pressure, etc.). In some embodiments, each segment is recorded over a time period that is sufficient to create a reliable distribution curve for statistics, for example, 5 minutes. In some embodiments, the recording of the baseline segments is performed over a period of 1 to 10 minutes where no arrhythmia events are present.

At 204, modified Shannon entropy is calculated with respect to each segment in the training set. For example, the difference in Shannon entropy of a pair in each three consecutive beats (or more beats with N−1 combination) is calculated (to reduce noise in the signal). The absolute value between each pair of beats is calculated, to provide a modified Shannon entropy value.

At 206, the distribution of modified Shannon entropy values is calculated for the entire segment. In some embodiments, the distribution is normalized for the average modified Shannon entropy, and the shape of this probability density function is calculated. In some embodiments, the distribution of the modified Shannon entropy of the segment is represented by estimation of statistical parameters.

At 208, a machine learning classifier is trained on the training set acquired and processed in steps 202-206.

At an inference stage 210, a real-time sample segment is taken over a relatively short period of time, e.g., 1 min. In some embodiments, the real-time recording of is performed over a period of 30 seconds to 5 minutes.

At 212, classifier 200 is applied to the real-time segment, to predict and/or detect an AF event, based, at least in part, on a distribution parameter of Shannon entropy and/or other HRV indices in the real-time segment.

At 214, in case of significant differences from the baseline distribution, the real-time measurements and processing may be repeated, e.g., between 2 and 6 times.

In some embodiments, the present disclosure employs, at least in part, the following definitions and assumptions for predicting and/or detecting AF events. For example, in the case of a finite set of consecutive beat intervals from a certain subject (time intervals between consecutive heart beats):

$$D=\{BI_i\}_{i=1}^{N}, BI_i \in \mathbb{R}, i \in \mathbb{Z}$$

The present modified Shannon entropy of order 2 may be defined as $\hat{S}_i^2(D)=||BI_{i-2}-BI_{i-1}|-|BI_{i-1}-BI_i||$, And for a general order M where $M \in \mathbb{N}$, $M>2$:

$\hat{S}_i^M = |\hat{S}_{i-1}^{M-1}| - |\hat{S}_i^{M=1}|$

It is further assumed that there exists a probability density function parametric family $Y = \{f_x(x,\theta) | \theta \in \Theta\}$, It should be noted that $\theta$ might be a multi-dimensional parameter set, for which distribution there will be used the notion $Y(\theta)$. Satisfying that for every possible set D of consecutive beat intervals from the same subject exists a $\theta \in \Theta$, such that $\hat{S}_i^M \sim Y(\theta) \forall BI \in D$.

For the probability density function $f_x(x, \theta)$, there is defined a "distribution width" function:

$W: Y \to \mathbb{R}^+$ where $W(f_x, (x, \theta))$ might be thought of as a generalized variance.

At the learning stage, the prediction algorithm works to estimate the characteristic $\theta$ for a certain subject in an arrhythmia-free time interval. For example, in the case of a learning set $D_l = \{BI_i\}_{i=1}^N, BI_i \in \mathbb{R} \; \forall i \in \mathbb{Z}$ satisfying $$\sum_{i=1}^N BI_i \approx 5 \text{ minutes,}$$

there is calculated an estimation for $\theta$, for which the notion $\hat{\theta}$ will be used. For $\hat{\theta}$ there is calculated the estimated distribution width $\hat{W} = W(f_x(x, \hat{\theta}))$ In the real-time calculation stage, the prediction algorithm defines a "narrow" distribution as:

$Y(\theta) | W(f_x(x,\theta)) < T(\hat{W})$,

Where, T(w) is a function $T: \mathbb{R} \to \mathbb{R}$ used in threshold determination. One might think of T(w) as a function determining how low a value of W should be to satisfy $P(w \leq W) < \alpha$. The real-time calculation set is then:

$D_{RT} = \{BI_i\}_{i=1}^N, BI_i \in \mathbb{R} \; \forall i \in \mathbb{Z}$, satisfying $$\sum_{i=1}^N BI_i \approx 1 \text{ minute.}$$

Accordingly, with every new beat, the prediction algorithm estimates the current $\hat{W}$ for n iterations. In some embodiments, n is a predetermined constant number, which can be chosen based on either heuristic methods, or through statistical analysis. If n or more consecutive real-time calculation sets are considered "narrow," it is considered as an "alarm." The implementation of the present prediction algorithm requires determination of an estimator for the distribution width W and a threshold estimating function T.

In some embodiments, the present disclosure can be implemented, for example, as a diagnostic system used for assessing the underlying etiology and/or the arrythmia profile of each patient's AF events, allowing personalized treatment. In some embodiments, the modified Shannon Entropy is used to separate patients into groups by Spectral Clustering (see, e.g., Andrew Y. Ng, Michael I. Jordan, Yair Weiss, "On spectral clustering: analysis and an algorithm", Proceedings of the 14th International Conference on Neural Information Processing Systems: Natural and Synthetic, Dec. 3-8, 2001). In some embodiments, the spectral clustering is based on a Laplace Kernel distance metric:

$$LaplaceDistance = e^{\frac{1}{N} \sum |Patient'sEntropy - GroupEntropy|},$$

where N is the length of the patient's entropy signal.

In some embodiments, the threshold estimating function, T, may be implemented using classic statistical estimators. In some embodiments, threshold estimating function, T, may be implemented using a machine learning algorithm.

In some embodiments, an exemplary detection algorithm according to some embodiments is based on the assumptions and definitions above, with the following additional definitions. For a set of N observations $D = \{X_i\}N_{i=1}^N$, the empirical distribution function is defined as:

$$F_N(x) = \frac{1}{N} \sum_{i=1}^N 1_{\{x > X_i\}}(x)$$

The estimators for the expectancy standard deviation are defined as the maximum likelihood estimators:

$$\hat{\mu} = \frac{1}{N} \sum_{i=1}^N X_i, \; \hat{\sigma} = \sqrt{\frac{1}{N-1} \sum_{i=1}^N (X_i^2 - \hat{\mu})}$$

The estimated normal distribution is defined as:

$$\hat{F}(x) = \Phi\left(\frac{x - \hat{\mu}}{\hat{\sigma}}\right)$$

where $\Phi$ is the cumulative distribution function of a normal standard random variable and the deviation from normality is defined as the Kolmogorov-Smirnov statistic:

$$KS(D) = \sup_x |F_N(x) - \hat{F}(x)|$$

Experimental Results

Atrial Fibrillation Prediction

Although under the present algorithm assumptions described above, the probability density function of the modified entropy exists, even if it is assumed that beat intervals are normally distributed, the use of a sum of absolute values in the modified entropy calculation might result in a different parametric family for the modified entropy. Moreover, the calculation of consecutive modified entropies used overlapping beat intervals, thus, one cannot assume $\hat{S}_i$ and $\hat{S}_{i+1}$ to be statistically independent. Thus, under different assumptions, different parametric families of distribution functions may be used.

Figure 3:
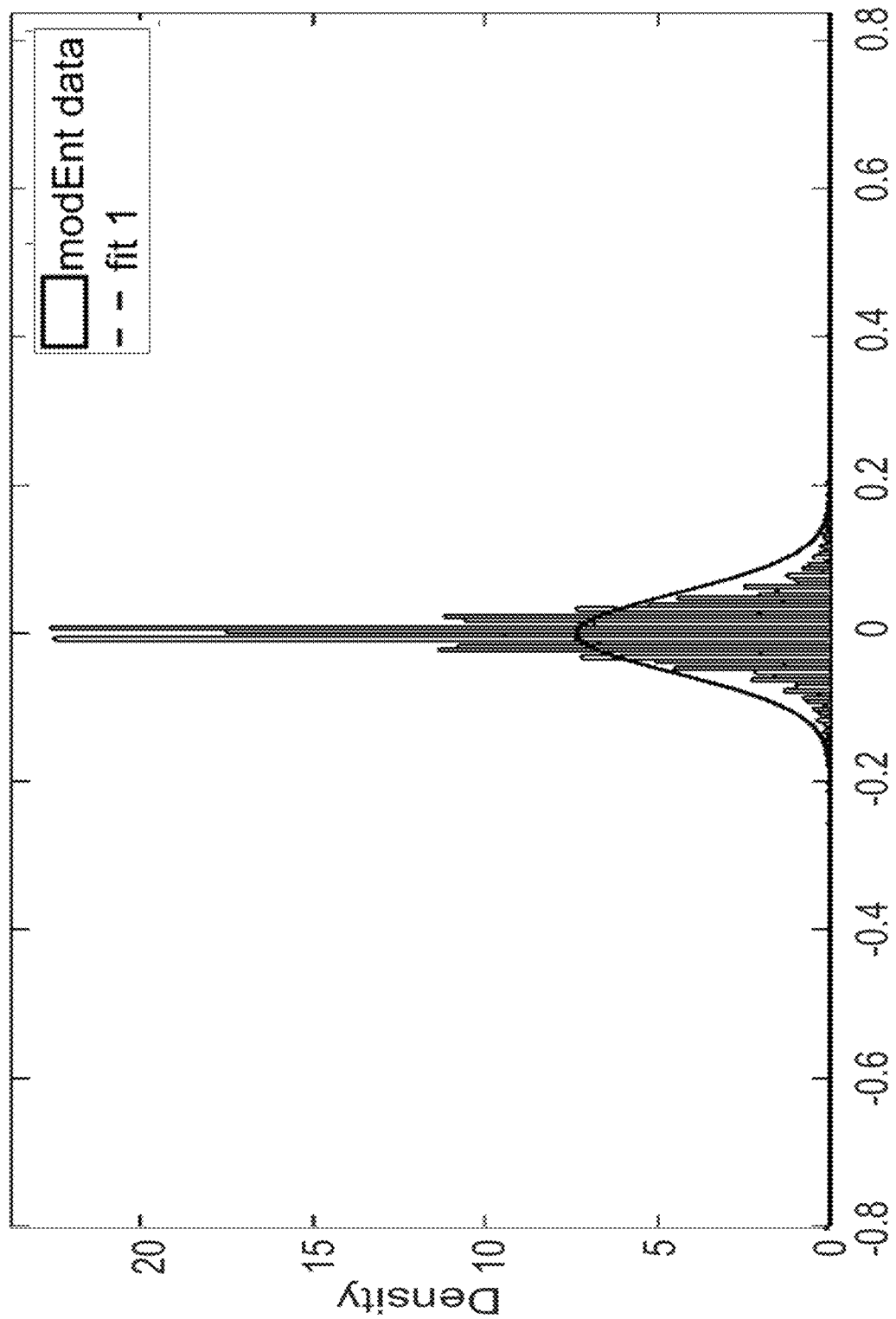
FIGS. 3, 4A-B, 5, 6, 7A-B, 8, 9A-B and 10 illustrate experimental results of a method for predicting and/or detecting atrial fibrillation or other irregular regularity, according an embodiment.

This theoretical result was clearly observed in numerical attempts to fit a normal distribution density function to sets of modified entropy samples, even when calculated from signals taken from the healthy subjects. FIG. 3 illustrates a density function fitting calculated and plotted by a Matlab Distribution fitting toolbox, in which a discrepancy between the histogram and the best fitting is evident. Accordingly, instead of finding a parametric family and truly calculating the distribution width from the estimated probability density function, in some embodiments, the algorithm is configured to try to estimate the distribution width directly from the samples, some examples for such an estimator are described below. In some embodiments the algorithm directly assesses the need for an alarm from the beat intervals sequence. Nevertheless, in some embodiments, the full process of distribution parametric family determination, parameter estimation and threshold estimation is utilized.

The "W" Estimator

For a set of N modified entropy samples $D=\{\hat{S}_i\}_{i=1}^N$, first calculate the empirical cumulative distribution function:

$$\hat{F}_n(\hat{S}) = \frac{1}{N}\sum_{i=1}^{N} 1_{\{\hat{S}_i < \hat{S}\}},$$

where $1_A$ is the indicator function of event A. Then, define a tail $$0 < \text{tail} < \frac{1}{2},$$

and find the samples $\hat{S}_{low}, \hat{S}_{high}$ satisfying:

$$\hat{S}_{low} = \max_{i=1,2,\dots N}\{\hat{S}_i\}, \text{ s.t.}: \hat{S}_i < \text{tail}$$

$$\hat{S}_{high} = \min_{i=1,2,\dots N}\{\hat{S}_i\}, \text{ s.t.}: \hat{S}_i > 1 - \text{tail}$$

The estimator to the distribution width is then:

$$W(D) = \hat{S}_{high} - \hat{S}_{low}$$

Figure 4A:
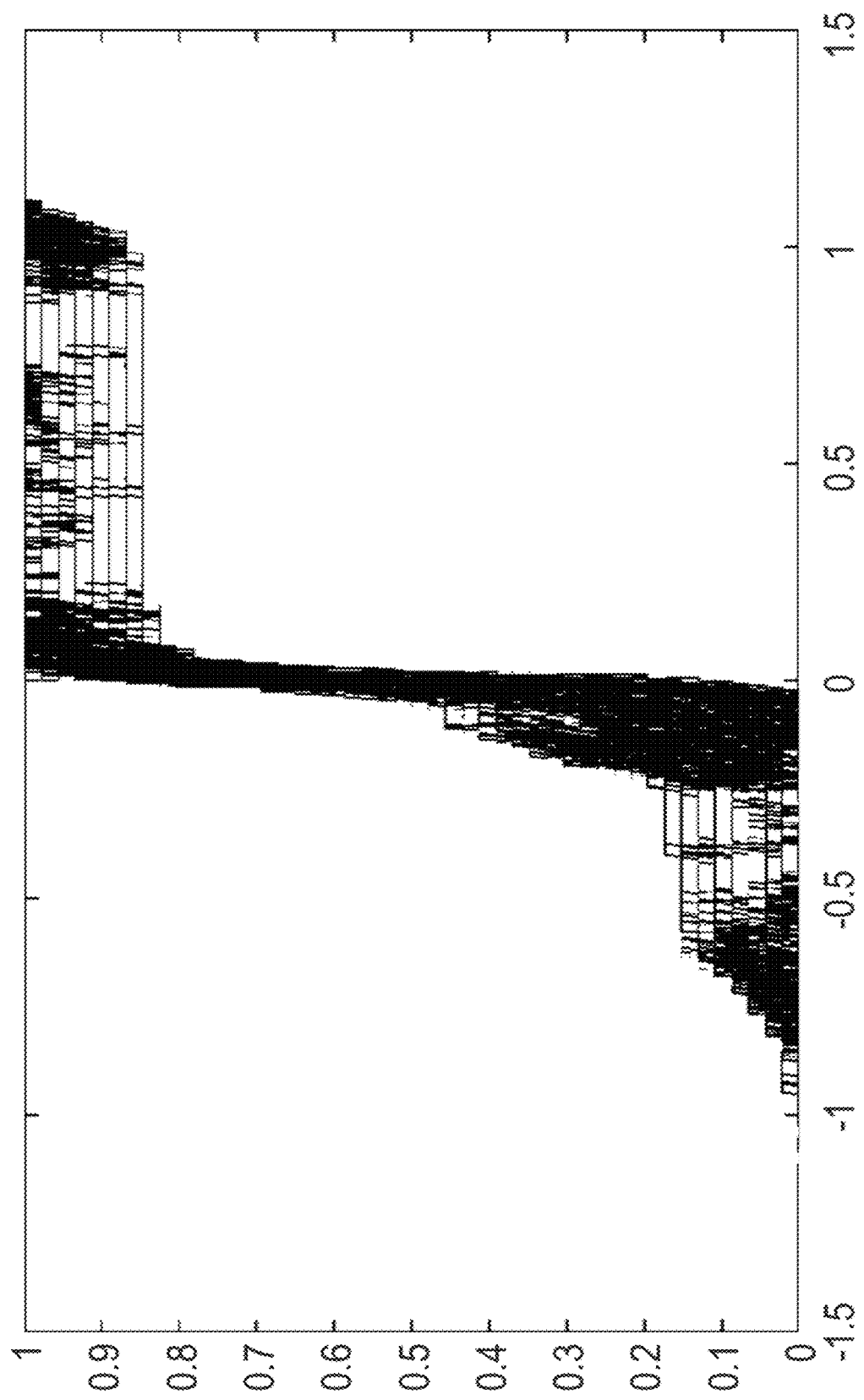
Figure 4B:
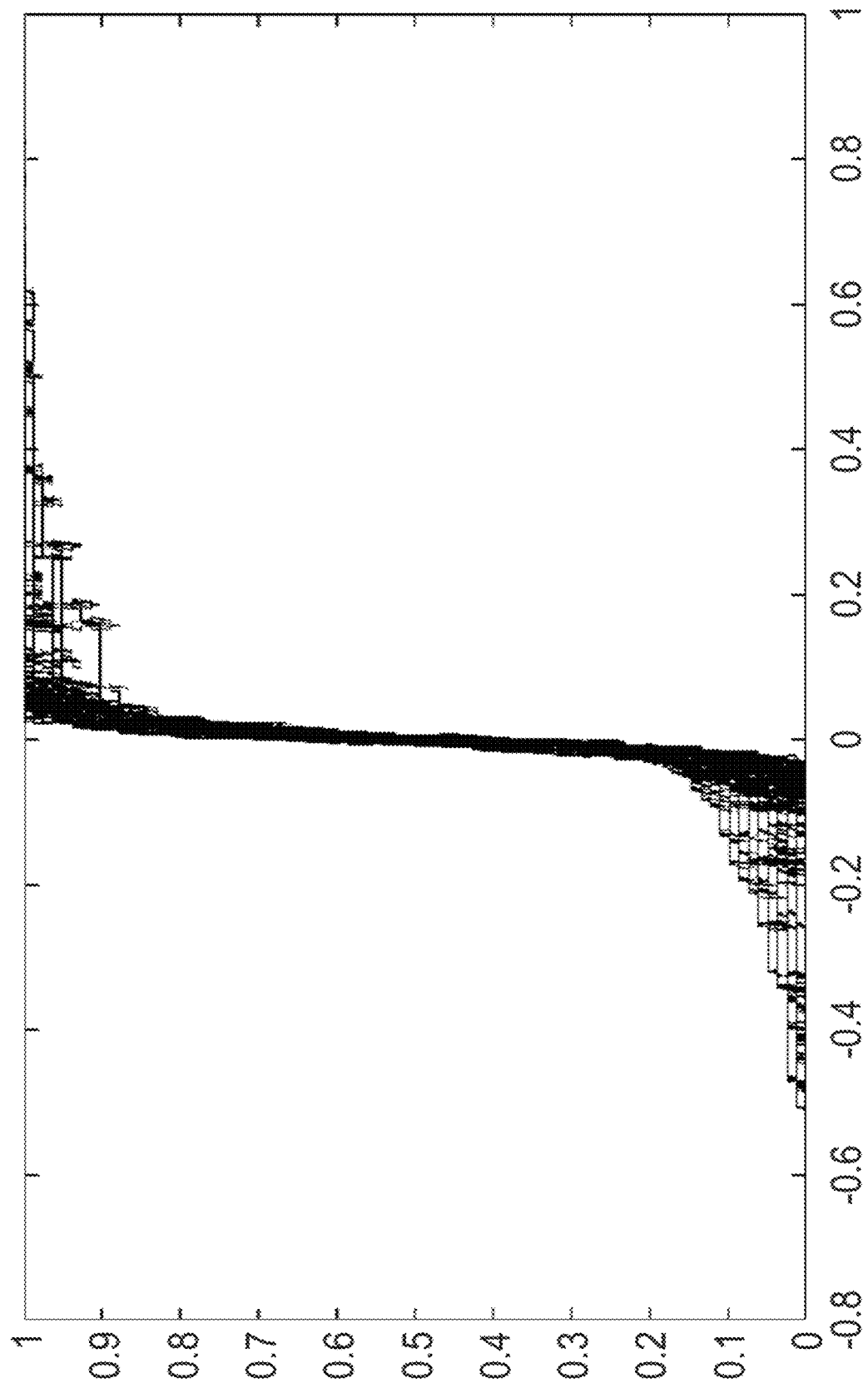

The use of empirical distribution functions yielded an interesting observation. FIG. 4 shows multiple empirical distribution functions of 1-minute sets of beat intervals from the same subject on the same figure. Difference can be noted between panel A, plotted using a recording from a subject with occasional AF episodes, and panel B, plotted using a recording from a healthy subject. In the healthy subject, it can qualitatively be seen that although some variability between the distribution of different sets exists, the variability is low and there are no distinct groups of curves. Conversely, in panel A, representing the AF patient's records, larger variability can be seen with 2 distinguishable groups of distribution width. Another, more subtle difference is the presence of some very narrow curves in the AF patient's results, which are absent in the healthy patient's results. These differences suggest that the empirical distribution width might hold the information needed to differentiate patients with and without AF.

The $\hat{\sigma}^2$ Estimator

A natural choice for a parameter to estimate distribution width is variance. The estimation of variance was made by the unbiased version of the maximum likelihood estimator:

$$\hat{\sigma}^2 = \frac{1}{n-1}\sum_{i=1}^{n}(x_i - \bar{x})^2.$$

Figure 5:
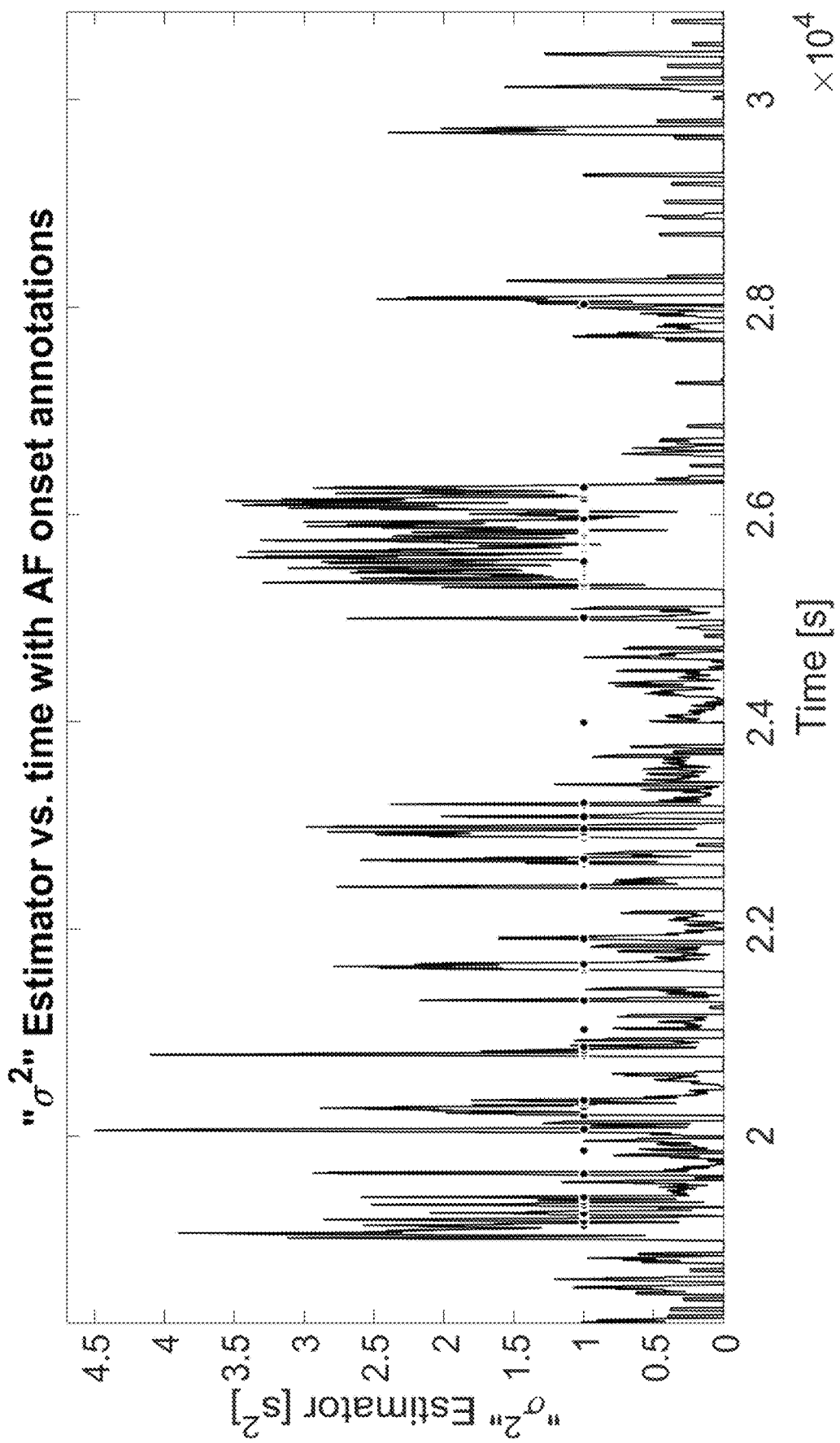
Figure 6:
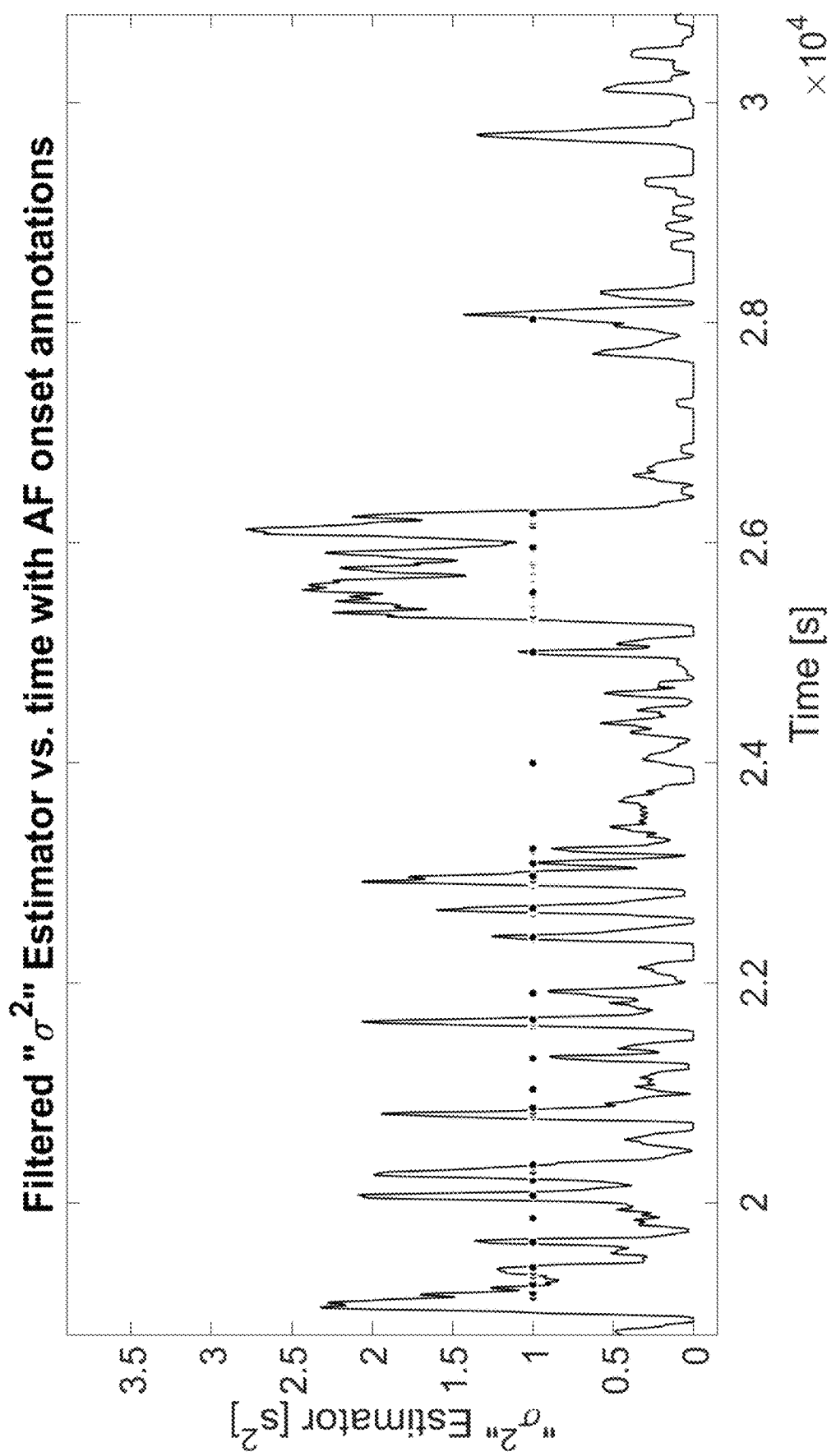

To reduce the noise, a moving average filter may be used, which produce a smoother signal. FIG. 5 shows a time plot with the $\hat{\sigma}^2$ estimator, while FIG. 6 shows the same time interval with the filtered estimator, wherein annotations of AF onset are marked by Xs. Higher values during arrhythmia episodes can be seen, with and the low values often preceding their onset.

An example of the threshold determination from a learning set $\{BI_i\}_{i=1}^N$, comprised of beat intervals from a patient, may be:

Calculate the modified entropy for each possible time point to yield a set of modified entropies $\{\hat{S}_i^2\}_{i=2}^{N-2}$. Calculate the average heart rate from the first minute of the sample, HR, and then, for each beat from the HR+1 beat and onward, calculate the distribution width estimation:

$$\hat{\sigma}_i^2 = \frac{1}{HR}\sum_{k=i-HR}^{i}\left(\hat{S}_k - \frac{1}{HR}\sum_{l=i-HR}^{i}\hat{S}_k\right)^2$$

to yield the set:

$$W = \{\hat{\sigma}_i^2\}_{HR+1}^{N},$$

Then calculate the mean of the variance estimator:

$$\overline{\hat{\sigma}^2} = \frac{1}{N-HR-1}\sum_{i=HR-1}^{N}\hat{\sigma}_i^2,$$

where the threshold is defined as:

$$T = \alpha\overline{\hat{\sigma}^2}, 0 < \alpha < 1.$$

Using this threshold, the preliminary definition for an alarm is:

$$\text{Alarms} = \{\hat{\sigma}^2 \in W | \hat{\sigma}^2 \leq T\}$$

Figure 7A:
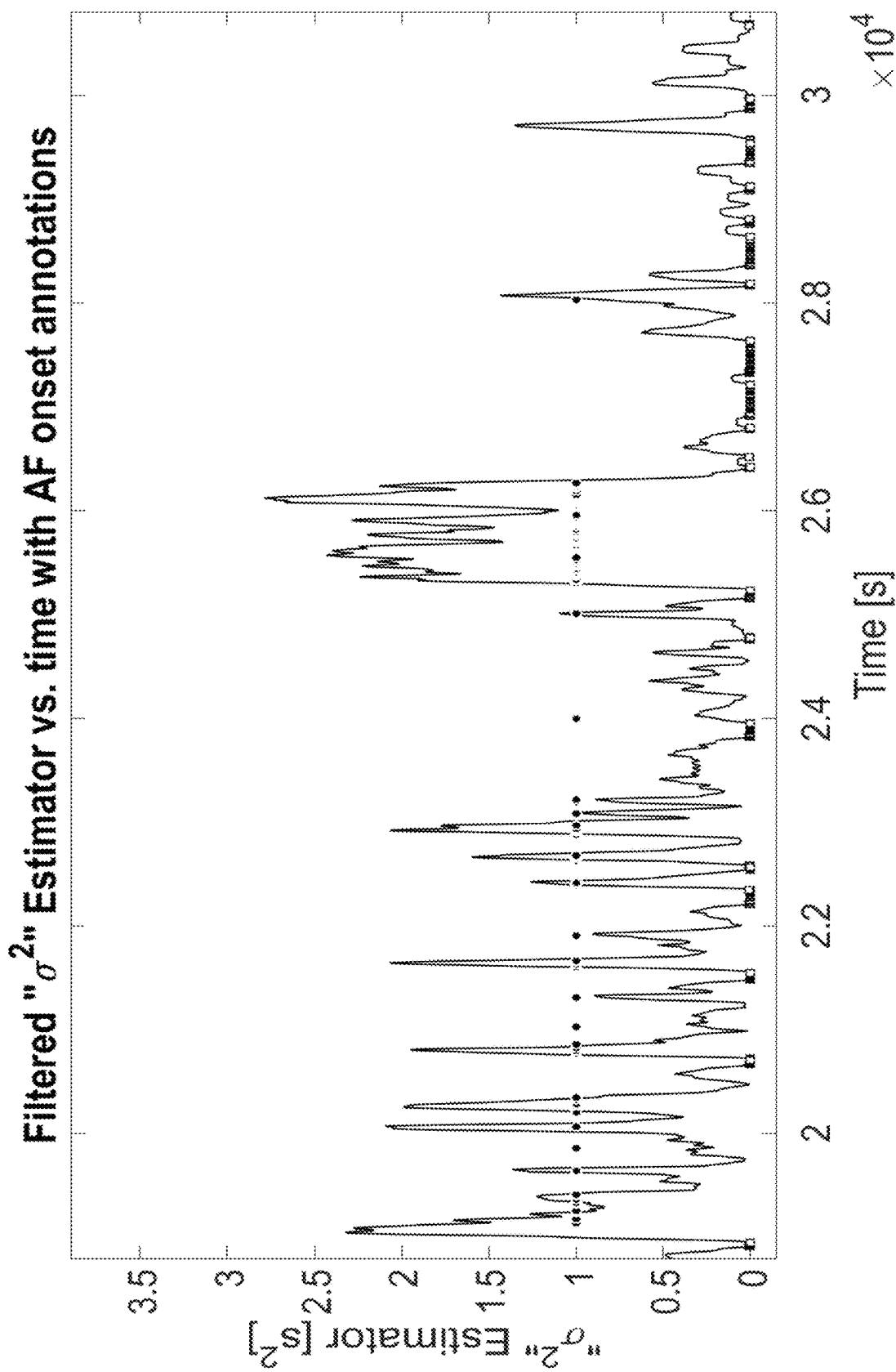
Figure 7B:
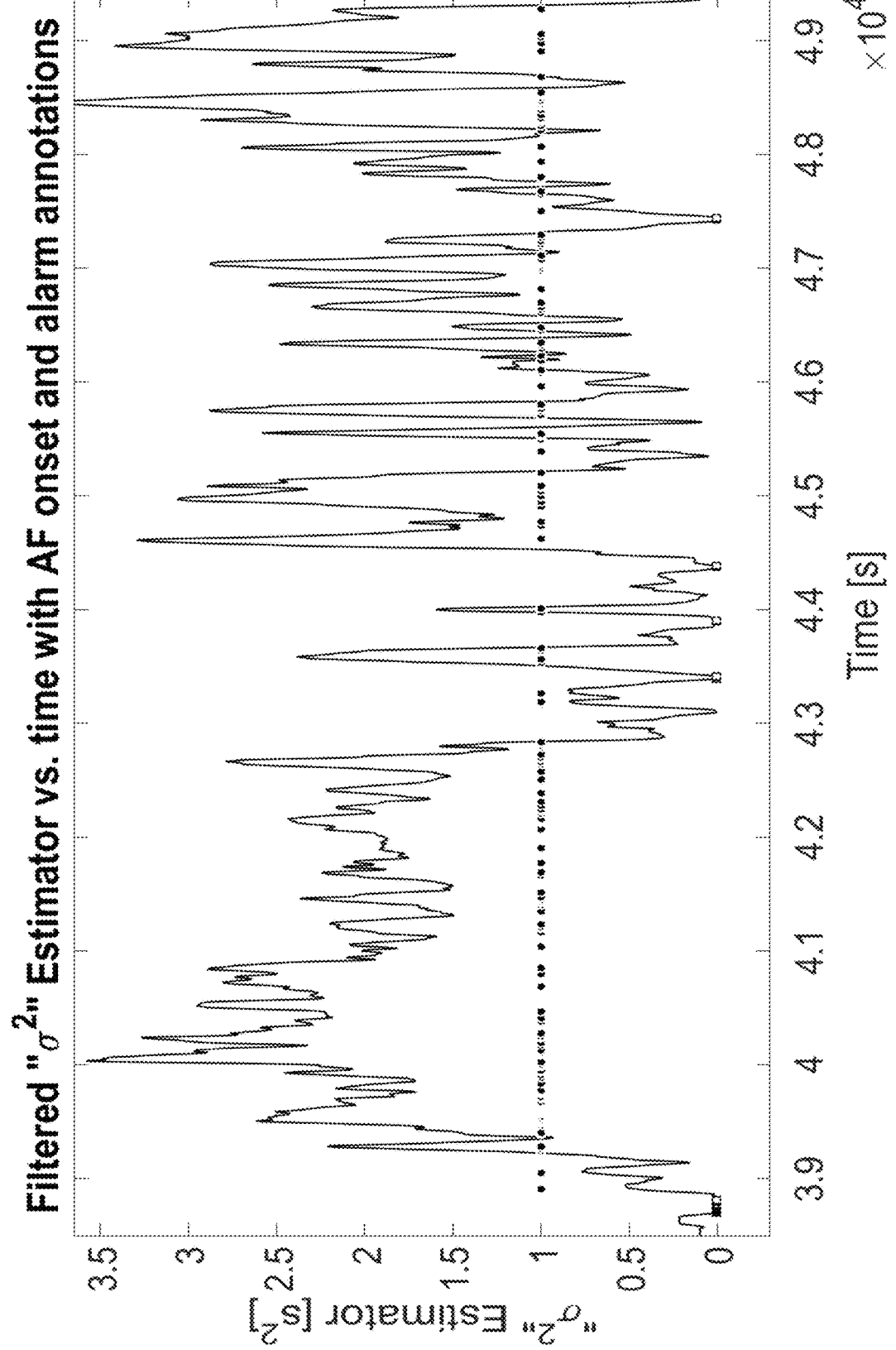

FIGS. 7A-7B shows a plot of the $\hat{\sigma}^2$ estimator after a running average filter in a representative time interval from an AF subject. Annotations of AF onset are marked by Xs, and alarms are marked by Xs of lighter shade.

FIG. 7A shows the same interval from the previous figures, now with the alarms (using $$\alpha = \frac{1}{200}\Big)$$

marked on the plot. FIG. 7B shows a similar plot of another time interval from the same subject.

Figure 8:
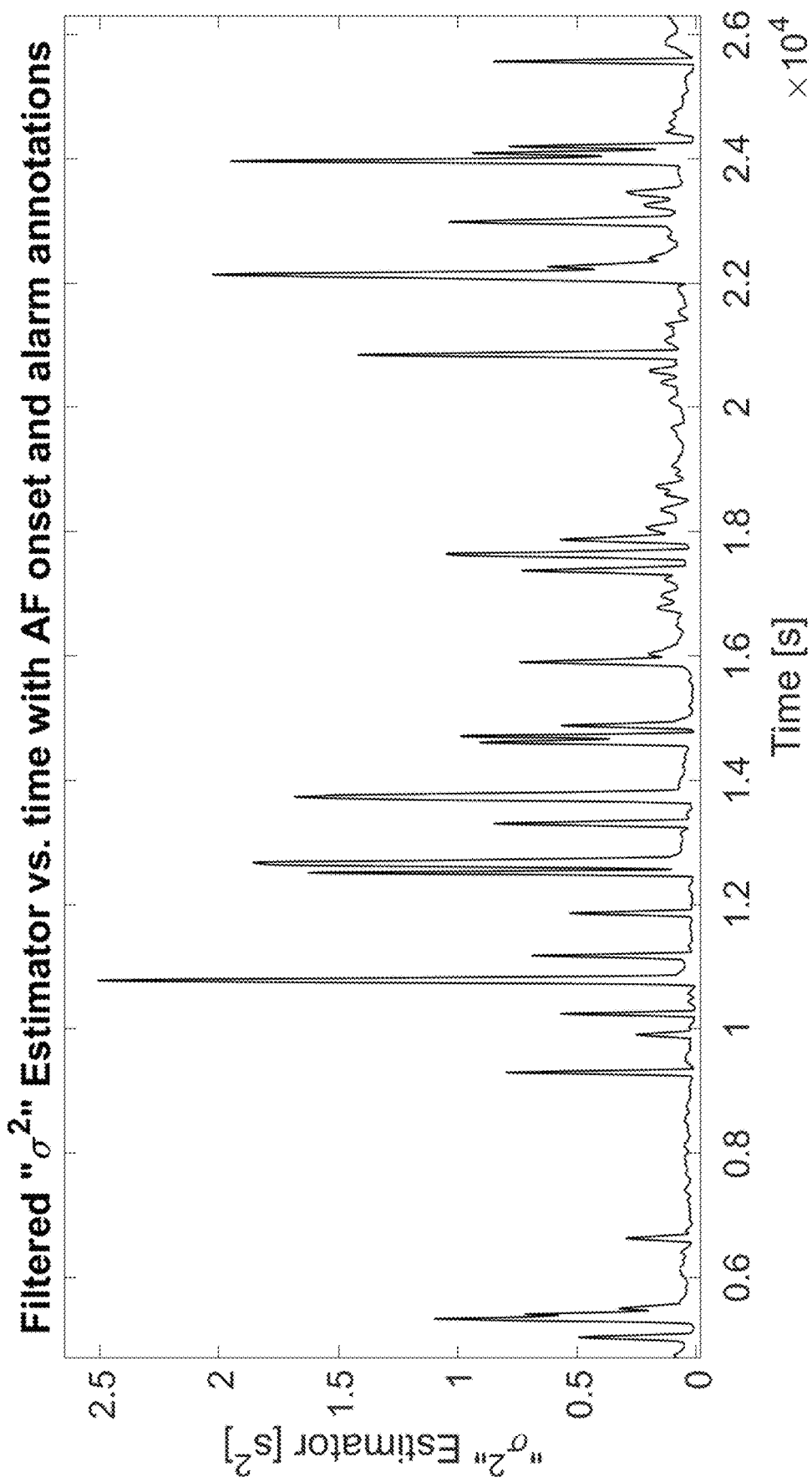

As a point of comparison, FIG. 8 shows a similar plot from a healthy subject. Even though some fluctuating does occur in healthy subjects, extremely low values are rare, and therefore in most of healthy subjects, no alarms are produced.

Atrial Fibrillation Patient Clustering

Figure 9A:
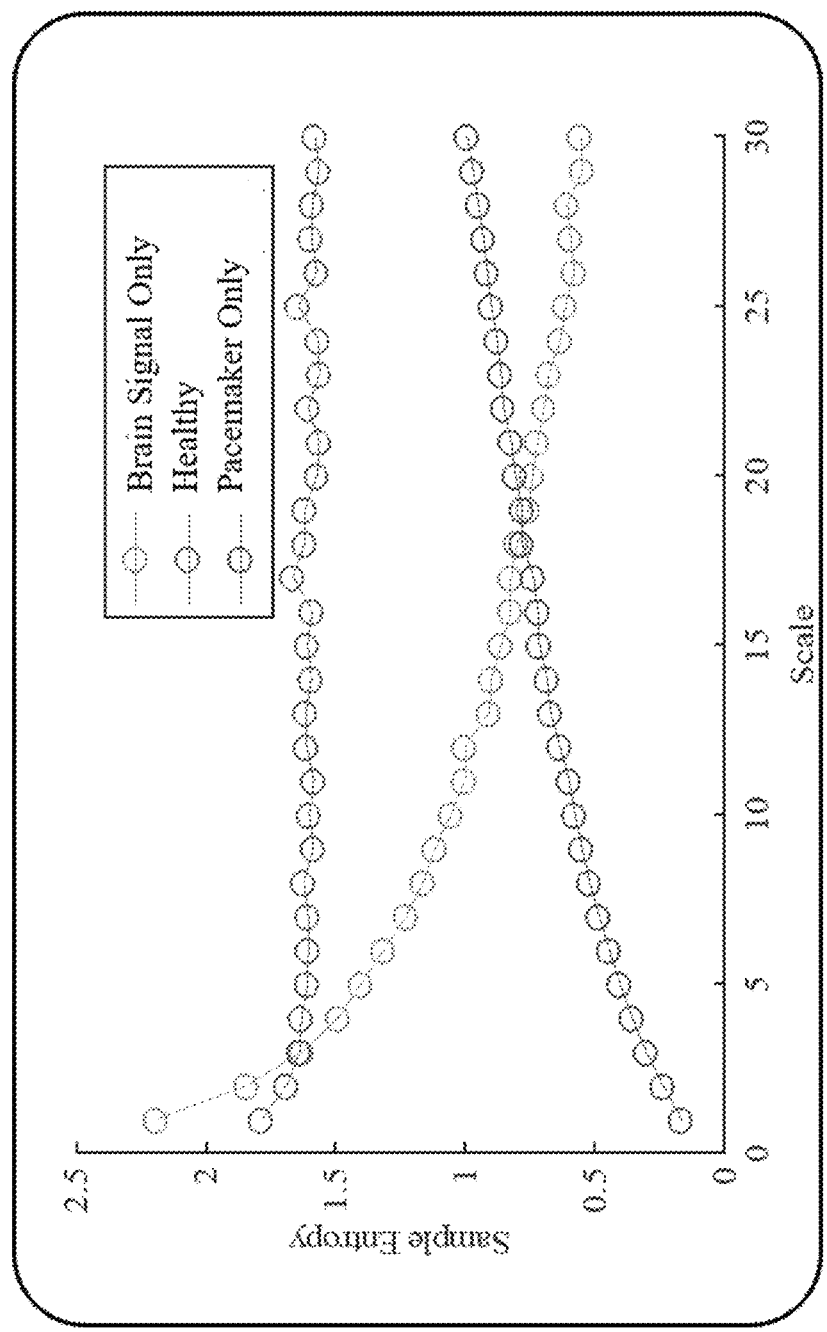
Figure 9B:
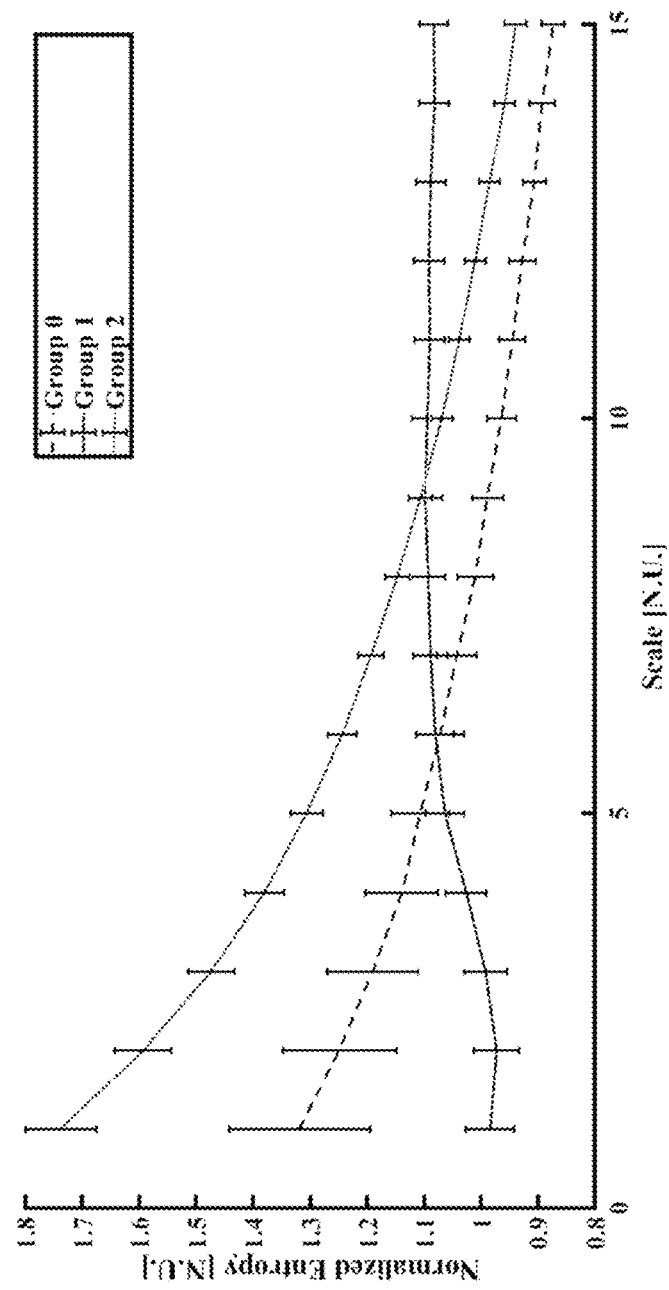

Using the Laplace Kernel distance metric for the Spectral Clustering algorithm, we clustered a patients cohort of both AF and healthy patients into 3 groups. Than we calculated the mean Multi-Scale Entropy (see, Costa M. at. Al., Physical review letters 89, no. 6 (2002): 068102) measure for each group. In FIGS. 9A-9B, one can see the correlation between the 3 groups from a controlled rabbits' experiment (FIG. 9A, see, e.g., Rosenberg, A. A. (2018), "Non-Invasive In-Vivo Analysis of Intrinsic Clock-Like Pacemaker Mechanisms: Decoupling Neural Input Using Heart Rate Variability Measurements" (master's thesis)) to that of the clustering (FIG. 9B). On further investigation, the clustering was found to group patients with similar pattern of arrhythmia.

In some embodiments, the clustering method herein is used to classify patients to groups to assist the personalization of medical treatment.

Atrial Fibrillation Detection

Atrial fibrillation is classically defined as " . . . a supraventricular arrhythmia characterized electrocardiographically by low-amplitude baseline oscillations (fibrillatory or f waves) and an irregularly irregular ventricular rhythm . . . " (see, Mann, Douglas L. et al., "Braunwald's Heart Disease: A Textbook of Cardiovascular Medicine." 10th edition. Philadelphia, Pa.: Elsevier/Saunders, 2015). Thus, in some embodiments, an algorithm identifying irregular irregularity of heart rate is used to detect atrial fibrillation episodes.

Figure 10:
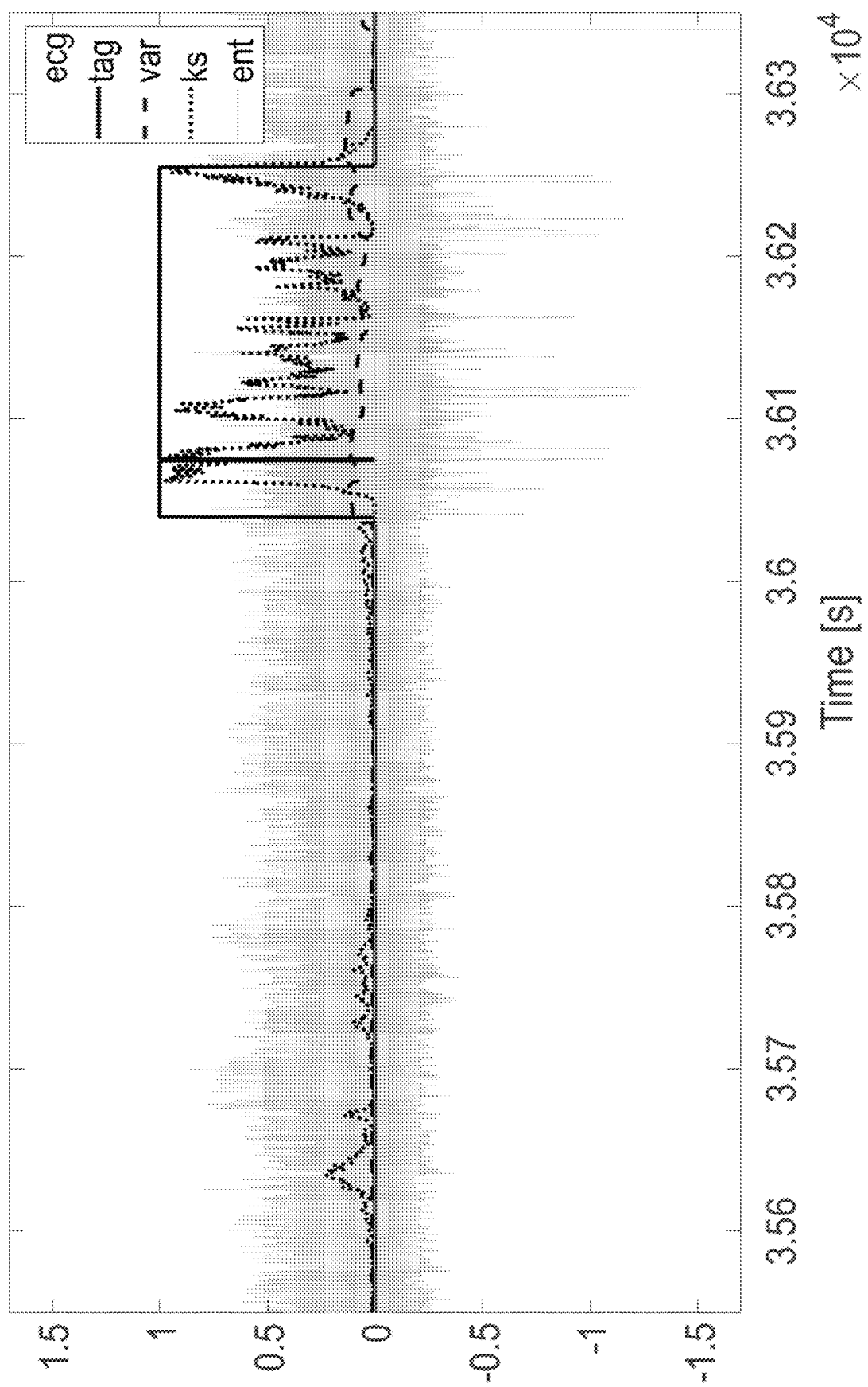

Heart rate irregularity show a strong correlation with the standard deviation of the modified Shannon entropy, but does not tell regular irregularity and irregular irregularity apart. The normality measure described above tell regular irregularity and irregular irregularity apart but is not specific for irregular irregularity and may give similar results in irregular irregularity and in normal sinus rhythm with complex dynamics. Thus, in some embodiments, both measures are used together to detect AF episodes. In FIG. 10 one may see that although both the standard deviation (denoted "var" in the legend) and the normality measure (denoted "ks" in the legend) can rise separately on non-AF times, they rise together only during the AF episodes.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claim is:

1. A method comprising:
    acquiring a data segment representing cardiac activity in a patient in real-time;
    calculating a modified Shannon entropy value as a difference in Shannon entropy between consecutive heartbeat intervals of the real-time data segment;
    calculating at least one parameter value representing distribution of entropy in said real-time data segment, selected from (i) a standard deviation of distribution of the modified Shannon entropy, and (ii) a normality measure KS, representing deviation from normal distribution of the modified Shannon entropy;
    using a Laplace Kernel distance metric to perform spectral clustering of patients, based on the entropy distribution, into groups having similar patterns of arrhythmia; and
    determining an etiology of a patient's Atrial Fibrillation (AF) event, based on the clustering.

2. The method of claim 1, wherein said calculating comprises calculating a distribution of said HRV parameter in all said data segments.

3. The method of claim 1, wherein each of said data segments is acquired over a period of between 1 and 10 minutes.

4. The method of claim 1, further comprising training, at a training stage, a machine learning classifier on a training set comprising:
    (i) said plurality of data segment, wherein at least some of said segments comprise cardiac activity reflecting an arrythmia event, and
    (ii) labels indicating the occurrence of an arrythmia event in said cardiac activity, wherein said data segments are labelled with said labels.

5. The method of claim 4, wherein said indicating is performed by applying, at an inference stage, said machine learning classifier to said signal, to indicate an AF event in said patient.

6. The method of claim 1, further comprising applying a clustering algorithm to said plurality of data segments, to cluster at least some of said data segments based, at least in part, on said HRV parameter.

7. The method of claim 6, wherein said clustering algorithm is a spectral clustering algorithm.

8. The method of claim 1, further comprising:
    calculating a difference in Shannon entropies between consecutive heartbeat intervals of the baseline signal, to obtain from each of said first data segments a value representing a modified Shannon entropy; and
    calculating the at least one first value as (i) a standard deviation of distribution of the modified Shannon entropy in the first data segments and (ii) a normality measure KS, representing deviation from normal distribution of the modified Shannon entropy.

9. The method of claim 1, wherein indicating an AF event in said patient comprises detecting a rise of the normality measure KS of the second segment in relation to the normality measure KS of the at least one first data segment.

10. The method of claim 9, wherein indicating an AF event in said patient further comprises detecting a rise of the standard deviation value of the second segment in relation to the standard deviation value of the at least one first data segment.

11. The method of claim 1, wherein the program instructions are further configured to calculate a difference between said first and second values by:
    calculating a normalized distribution $\tilde{F}(x)$ of the entropy distributions of the at least one first segment and second segment;
    calculating (206) a standard deviation of the normalized distributions; and
    calculating a normality measure KS, representing a deviation from normal distribution of the modified Shannon entropy distributions.

12. The method of claim 11, further comprising calculating a difference between said first and second values by calculating difference in the normality measure KS and the standard deviation.

13. The method of claim 11, further comprising detecting an AF event based on a rise of both the normality measure and the standard deviation.

14. The method of claim 11, further comprising calculating the normality measure KS based on a Kolmogorov-Smirnov (KS) statistic.

15. A system comprising:
    at least one hardware processor; and
    a non-transitory computer-readable storage medium having stored thereon program instructions, the program instructions executable by the at least one hardware processor to:
        acquire a data segment representing cardiac activity in a patient in real time;

calculate a modified Shannon entropy value as a difference in Shannon entropy between consecutive heartbeat intervals of the real-time data segment;

calculate at least one parameter value representing distribution of entropy in said real-time data segment, selected from (i) a standard deviation of distribution of the modified Shannon entropy, and (ii) a normality measure KS, representing deviation from normal distribution of the modified Shannon entropy;

use a Laplace Kernel distance metric to perform spectral clustering of patients, based on the entropy distribution, into groups having similar patterns of arrhythmia; and determine an etiology of a patient's Atrial Fibrillation (AF) event, based on the clustering.

16. The system of claim 15, wherein said program instructions are further executable to train, at a training stage, a machine learning classifier on a training set comprising:

(i) said plurality of data segment, wherein at least some of said segments comprise cardiac activity reflecting an arrythmia event, and (ii) labels indicating the occurrence of an arrythmia event in said cardiac activity.

17. The system of claim 15, wherein said indicating comprises at least one of detecting an ongoing AF event, and predicting an upcoming AF event.

18. The method of claim 1 further comprising indicating the AF event in said patient by detecting (i) a rise of the normality measure KS of the real-time data segment, and (ii) a rise of the standard deviation value of the real-time data segment.

* * * * *